(12) United States Patent
Kochhar et al.

(10) Patent No.: US 9,474,534 B2
(45) Date of Patent: Oct. 25, 2016

(54) FORMULATIONS OF ORGANIC COMPOUNDS

(71) Applicants: Charu Kochhar, Basel (CH); Jacques Quinton, Waldinghoffen (FR)

(72) Inventors: Charu Kochhar, Basel (CH); Jacques Quinton, Waldinghoffen (FR)

(73) Assignee: Novartis AG (CH)

( * ) Notice: Subject to any disclaimer, the term of this patent is extended or adjusted under 35 U.S.C. 154(b) by 0 days.

(21) Appl. No.: 14/771,908

(22) PCT Filed: Mar. 4, 2014

(86) PCT No.: PCT/IB2014/059424
§ 371 (c)(1),
(2) Date: Sep. 1, 2015

(87) PCT Pub. No.: WO2014/136048
PCT Pub. Date: Sep. 12, 2014

(65) Prior Publication Data
US 2016/0015643 A1    Jan. 21, 2016

Related U.S. Application Data

(60) Provisional application No. 61/773,492, filed on Mar. 6, 2013.

(51) Int. Cl.
| | | |
|---|---|---|
| *A61K 31/5377* | (2006.01) | |
| *A61K 9/16* | (2006.01) | |
| *A61K 9/42* | (2006.01) | |
| *A61K 31/231* | (2006.01) | |
| *A61B 17/12* | (2006.01) | |
| *A61K 9/20* | (2006.01) | |
| *A61J 3/10* | (2006.01) | |
| *A61M 25/10* | (2013.01) | |

(52) U.S. Cl.
CPC ..... *A61B 17/12136* (2013.01); *A61B 17/1204* (2013.01); *A61B 17/12109* (2013.01); *A61J 3/10* (2013.01); *A61K 9/1617* (2013.01); *A61K 9/2009* (2013.01); *A61K 9/2013* (2013.01); *A61K 9/2018* (2013.01); *A61K 9/2027* (2013.01); *A61K 9/2054* (2013.01); *A61K 9/2077* (2013.01); *A61K 9/2095* (2013.01); *A61K 31/231* (2013.01); *A61K 31/5377* (2013.01); *A61M 25/1002* (2013.01); *A61B 2017/12068* (2013.01); *A61B 2017/12086* (2013.01)

(58) Field of Classification Search
None
See application file for complete search history.

(56) References Cited

FOREIGN PATENT DOCUMENTS

WO    2007/084786 A1    7/2007

OTHER PUBLICATIONS

Bendell Johanna C et al: "Phase I, dose-escalation study of BKM120, an oral pan-class I PI3K inhibitor, in patients with advanced solid tumors", Journal O Clinical Oncology, American Society of Clinical Oncology, US, vol. 30, No. 3, Jan. 1, 2012, pp. 282-290.

*Primary Examiner* — James D Anderson
*Assistant Examiner* — Gregg Polansky
(74) *Attorney, Agent, or Firm* — Sandra Rueck

(57) ABSTRACT

The present invention relates to solid pharmaceutical compositions comprising the phosphatidylinositol 3-kinase inhibitor compound 4-(trifluoromethyl)-5-(2,6-dimorpholinopyrimidin-4-yl)pyridin-2-amine or a pharmaceutically acceptable salt thereof, sodium stearyl fumarate, and optionally at least one additional pharmaceutically acceptable carrier. The present invention also relates to the processes for their preparation and to their use as medicaments for the treatment of cancer.

14 Claims, 5 Drawing Sheets

Upper Punches  Lower punches

Upper Punches  Lower punches

FORMULATIONS OF ORGANIC COMPOUNDS

TECHNICAL FIELD

The present invention relates to solid pharmaceutical compositions comprising the phosphatidylinositol 3-kinase inhibitor compound 4-(trifluoromethyl)-5-(2,6-dimorpholinopyrimidin-4-yl)pyridin-2-amine or a pharmaceutically acceptable salt thereof, sodium stearyl fumarate, and optionally at least one additional pharmaceutically acceptable carrier. The present invention also relates to the processes for their preparation and to their use as medicaments for the treatment of cancer.

BACKGROUND OF THE DISCLOSURE

In normal cells, the phosphatidylinositol-3-kinase (PI3K) is a regulator of multiple cellular functions, including protein synthesis and glucose metabolism, cell survival and growth, proliferation, cellular resilience and repair, cell migration, and angiogenesis. There is substantial evidence that in many tumors the PI3K signaling pathway is constitutively activated. Activation of the PI3K pathway via amplifications or mutations in the catalytic subunit (PIK3CA) or inactivation of negative regulators (e.g., PTEN) results in constitutive signaling and oncogenicity. Deregulation of the PI3K pathway is established to be one of the most frequent occurrences in various human cancers, including but not limited to pancreatic cancer, breast cancer and lung cancer.

The specific pyrimidine derivative compound of formula (I)

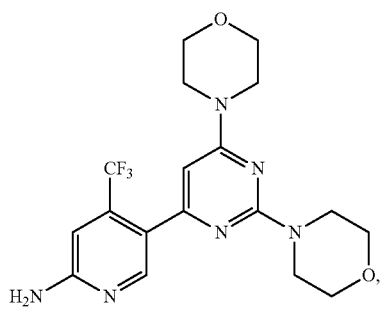

(I)

and its pharmaceutically acceptable salts are phosphatidylinositol-3-kinase (PI3K) inhibitors which may be used for the treatment of cancer. The compound of formula (I) has the chemical name 4-(trifluoromethyl)-5-(2,6-dimorpholinopyrimidin-4-yl)pyridin-2-amine. These compounds and their preparation are disclosed in WO2007/084786. Such pyrimidine derivative is proven to be an effective PI3K inhibitor, e.g. WO2007/084786 and S. Maira et al, Molecular Cancer Therapeutics 11:317-328 (2012), that displays broad activity against a large panel of cultured human cancer cell lines.

Administration of pharmaceutical agents via the oral route is advantageous to other administration routes (e.g., parenteral) because it allows self-administration by patients instead of administration by a physician, nurse or paramedical personnel.

However, the PI3K inhibitor compound 4-(trifluoromethyl)-5-(2,6-dimorpholinopyrimidin-4-yl)pyridin-2-amine and its pharmaceutically acceptable salts are difficult to formulate due to its physiochemical properties, and it is not trivial to make solid pharmaceutical compositions in a reliable and robust way. For example, this compound exhibits poor flowability and significant sticking tendency. Due to these physiochemical properties, it has been found that this compound is difficult to formulate into pharmaceutical compositions. Even when formulated with common lubricants (e.g., magnesium stearate), the compound remains sticky and is difficult to handle in a tableting machine. Other formulations of this compound showed poor compressibility. Accordingly, a suitable and robust solid pharmaceutical composition overcoming the above problems related to the properties of the compound 4-(trifluoromethyl)-5-(2,6-dimorpholinopyrimidin-4-yl)pyridin-2-amine and its pharmaceutically acceptable salts needs to be developed.

Surprisingly, it has been found that a robust solid pharmaceutical composition comprising the compound 4-(trifluoromethyl)-5-(2,6-dimorpholinopyrimidin-4-yl)pyridin-2-amine or a pharmaceutically acceptable salt thereof can be prepared conveniently using roller compaction when sodium stearyl fumarate is used as a lubricant. These solid pharmaceutical compositions overcome the foregoing problems and exhibits no or minimal sticking tendency and sufficient compressibility and hardness for the reliable and robust delivery of this compound or its pharmaceutically acceptable salts to patients in need thereof.

SUMMARY OF THE DISCLOSURE

The present invention relates to a roller compacted solid pharmaceutical composition comprising (a) the compound 4-(trifluoromethyl)-5-(2,6-dimorpholinopyrimidin-4-yl)pyridin-2-amine or a pharmaceutically acceptable salt thereof, (b) sodium stearyl fumarate, and (c) optionally at least one additional pharmaceutically acceptable carrier.

In one embodiment, the present invention provides a roller compacted solid pharmaceutical composition comprising (a) the compound 4-(trifluoromethyl)-5-(2,6-dimorpholinopyrimidin-4-yl)pyridin-2-amine or a pharmaceutically acceptable salt thereof, (b) sodium stearyl fumarate, and (c) optionally at least one additional pharmaceutically acceptable carrier, wherein the pharmaceutical composition contains a plurality of granules having an internal phase and an external phase, and wherein said internal phase and external phase of the granules both include sodium stearyl fumarate.

In one embodiment, the present invention provides a solid pharmaceutical composition comprising (a) the compound 4-(trifluoromethyl)-5-(2,6-dimorpholinopyrimidin-4-yl)pyridin-2-amine or a pharmaceutically acceptable salt thereof, (b) sodium stearyl fumarate, and (c) optionally at least one additional pharmaceutically acceptable carrier, wherein said composition is prepared by roller compaction, and wherein said pharmaceutical composition is in the form of a tablet.

In one embodiment, the present invention provides a solid dosage form comprising a roller compacted solid pharmaceutical composition comprising (a) the compound 4-(trifluoromethyl)-5-(2,6-dimorpholinopyrimidin-4-yl)pyridin-2-amine or a pharmaceutically acceptable salt thereof, (b) sodium stearyl fumarate, and (c) optionally at least one additional pharmaceutically acceptable carrier. Preferably, the solid dosage form is a film-coated tablet.

In one embodiment, the present invention is related to a process for the manufacture of a solid pharmaceutical composition comprising the steps of roller compacting the compound 4-(trifluoromethyl)-5-(2,6-dimorpholinopyrimidin-4-yl)pyridin-2-amine or a pharmaceutically acceptable salt thereof together with sodium stearyl fumarate and optionally at least one additional pharmaceutically acceptable carrier, milling the compacted material to form a plurality of granules, and blending the granules with sodium stearyl fumarate and optionally at least one additional pharmaceutically acceptable carrier, and optionally compressing the final blend into a tablet.

In one embodiment, the present invention is related to a process for the manufacture of a solid pharmaceutical composition comprising the steps of:
(a) blending the compound 4-(trifluoromethyl)-5-(2,6-dimorpholinopyrimidin-4-yl)pyridin-2-amine or a pharmaceutically acceptable salt thereof together with sodium stearyl fumarate and optionally at least one additional pharmaceutically acceptable carrier,
(b) sieving or screening the blended material,
(c) roller compacting the sieved or screened material to form a compacted material,
(d) milling the compacted material to form a plurality of granules,
(e) blending the granules with sodium stearyl fumarate and optionally at least one additional pharmaceutically acceptable carrier to form a final mixture, and
(f) optionally compressing the final blend into a tablet.

In one embodiment, the present invention is related to a process for the manufacture of a film-coated tablet comprising the steps of roller compacting the compound 4-(trifluoromethyl)-5-(2,6-dimorpholinopyrimidin-4-yl)pyridin-2-amine or a pharmaceutically acceptable salt thereof together with sodium stearyl fumarate and optionally at least one additional pharmaceutically acceptable carrier, milling the compacted material to form a plurality of granules, and blending the granules with sodium stearyl fumarate and optionally at least one additional pharmaceutically acceptable carrier, compressing the final blend into a tablet, and optionally applying a film-coat to the tablet.

In one embodiment, the present invention is related to a process for the manufacture of a film-coated tablet comprising the steps of:
(a) blending the compound 4-(trifluoromethyl)-5-(2,6-dimorpholinopyrimidin-4-yl)pyridin-2-amine or a pharmaceutically acceptable salt thereof together with sodium stearyl fumarate and optionally at least one additional pharmaceutically acceptable carrier,
(b) sieving or screening the blended material,
(c) roller compacting the sieved or screened material to form a compacted material,
(d) milling the compacted material to form a plurality of granules,
(e) blending the granules with sodium stearyl fumarate and optionally at least one additional pharmaceutically acceptable carrier to form a final mixture, and
(f) compressing the final blend into a tablet, and
(g) applying a film-coat to the tablet.

In one embodiment, the present invention provides the roller compacted solid pharmaceutical composition of the present invention for use for the treatment of cancer.

In one embodiment, the present invention provides the use of a roller compacted solid pharmaceutical composition of the present invention for the manufacture of a medicament for the treatment of cancer.

In one embodiment, the present invention provides a method for the treatment of cancer comprising administering a a roller compacted solid pharmaceutical composition of the present invention comprising a therapeutically effective amount of the compound 4-(trifluoromethyl)-5-(2,6-dimorpholinopyrimidin-4-yl)pyridin-2-amine or a pharmaceutically acceptable salt thereof to a patient suffering from such cancer.

DETAILED DESCRIPTION OF THE DISCLOSURE

Figure 1:
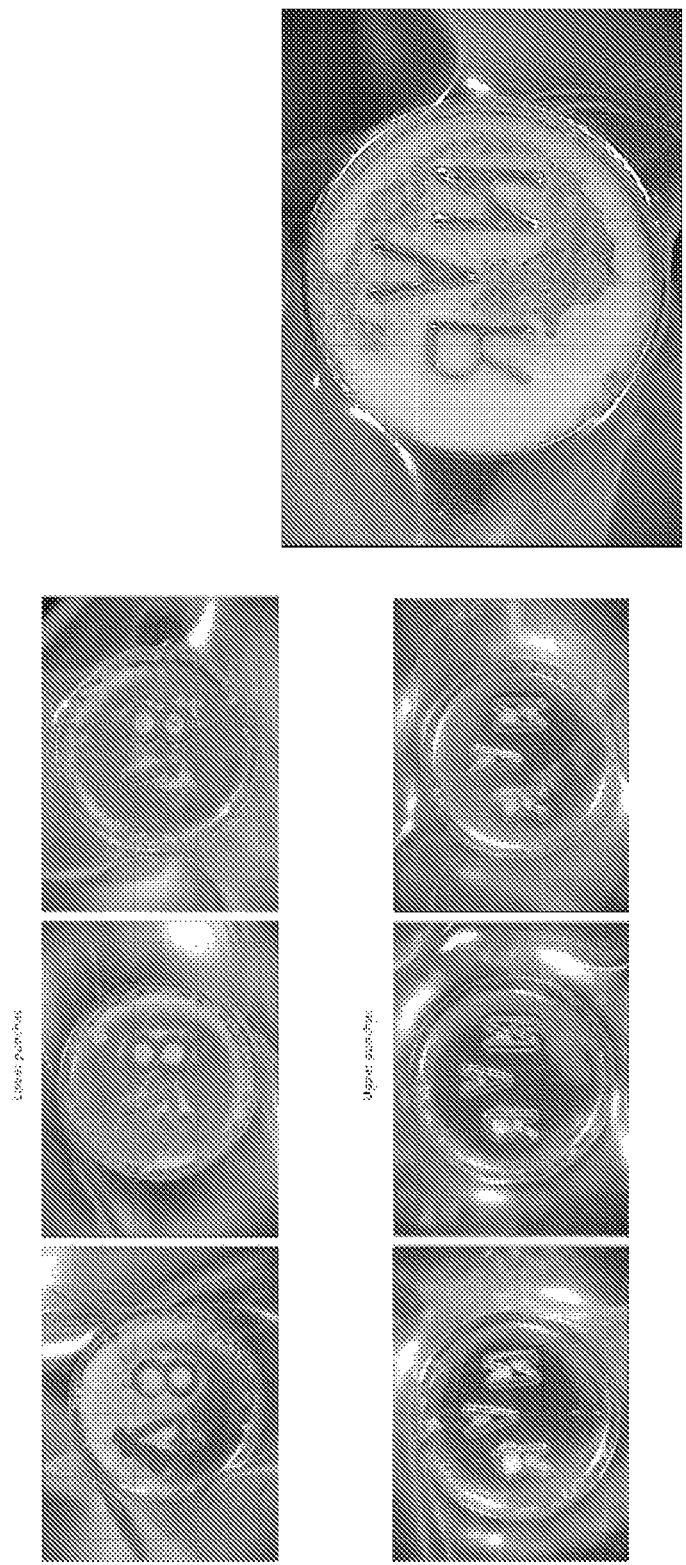
FIG. 1 shows photographic images displaying the significant tablet sticking and picking (i.e., adherence of powder to the tablet punch surface) of a previous direct compression pharmaceutical composition comprising the compound 4-(trifluoromethyl)-5-(2,6-dimorpholinopyrimidin-4-yl)pyridin-2-amine hydrochloride salt and the lubricant magnesium stearate vegetable (2% by weight relative to the weight of the overall composition), to the tablet punch.

The present invention relates to a roller compacted solid pharmaceutical composition comprising (a) the compound 4-(trifluoromethyl)-5-(2,6-dimorpholinopyrimidin-4-yl)pyridin-2-amine or a pharmaceutically acceptable salt thereof, (b) sodium stearyl fumarate, and (c) optionally at least one additional pharmaceutically acceptable carrier. In particular, the present invention provides oral dosage forms comprising such solid pharmaceutical composition.

As used herein, the following terms have the meanings ascribed to them unless specified otherwise:

The term "pharmaceutical composition" or "formulation" means a physical mixture containing a therapeutic compound to be administered to a subject, e.g., a human, in order to prevent, treat or control a particular disease or condition affecting the subject. The term "pharmaceutical composition" or "formulation" as used herein, for example, also encompasses an intimate physical mixture formed at high temperature and pressure.

The term "pharmaceutically acceptable" refers to those compounds, materials, compositions, carriers, and/or dosage forms, which are, within the scope of sound medical judgment, suitable for contact with the tissues of a subject, especially humans, without excessive toxicity, irritation, allergic response and other problem complications commensurate with a reasonable benefit/risk ratio.

The terms "pharmaceutically acceptable carrier" and "carrier" refer to any inert and pharmaceutically acceptable material that has substantially no biological activity, and makes up a substantial part of the formulation.

The term "therapeutically effective amount" refers to an amount or concentration which is effective in reducing, eliminating, treating, preventing or controlling the symptoms of a disease or condition affecting a subject. The term "controlling" is intended to refer to all processes wherein there may be slowing, interrupting, arresting or stopping of the progression of the diseases and conditions affecting the mammal. However, "controlling" does not necessarily indicate a total elimination of all disease and condition symptoms.

The phrase "oral dosage form" refers to a pharmaceutical composition that is prepared for administration to a subject through the oral route of administration. Examples of known oral dosage forms, include without limitation, tablets, capsules, caplets, powders, pellets, granules, solutions, suspensions, solutions and solution pre-concentrates, emulsions and emulsion pre-concentrates, etc. In some aspects, powders, pellets, granules and tablets may be coated with a suitable polymer or a conventional coating material to achieve, for example, greater stability in the gastrointestinal tract, or to achieve the desired rate of release. Moreover, capsules containing a powder, pellets or granules may be further coated. Tablets may be scored to facilitate division of dosing. Alternatively, the dosage forms of the present invention may be unit dosage forms wherein one unit dosage form is intended to deliver one therapeutic dose per administration or wherein multiple unit dosage forms are intended to deliver the total therapeutic dose per administration.

The term "treat", "treating", or "treatment" includes prophylactic (preventive) and/or therapeutic treatment as well as the delay of progression of a disease or disorder. The term "delay of progression" as used herein means administration of the pharmaceutical composition to a subject being in a pre-stage or in an early phase of the cancer to be treated, in which patients for example a pre-form of the corresponding disease is diagnosed or which a subject is in a condition, e.g. during a medical treatment, under which it is likely that a corresponding disease will develop. Preferably, the term "treat", "treating", or "treatment" refers to therapeutic treatment as well as the delay of progression of a disease or disorder.

The terms "administration," and "administering" refer to the manner in which a therapeutic compound is presented to a subject.

The term "oral administration" represents any method of administration in which a therapeutic compound can be administered through the oral route by swallowing, chewing, or sucking an oral dosage form. Solid oral dosage forms are traditionally intended to substantially release and or deliver the active agent in the gastrointestinal tract beyond the mouth and/or buccal cavity. Examples of solid dosage forms include conventional tablets, capsules, caplets, etc.

The term "subject" or "patient" is intended to include animals. Examples of subjects include mammals, e.g., humans, dogs, cows, horses, pigs, sheep, goats, cats, mice, rabbits, rats, and transgenic non-human animals. In certain embodiments, the subject is a human, e.g., a human suffering from, at risk of suffering from, or potentially capable of suffering from cancers.

The terms "comprising" and "including" are used herein in their open-ended and non-limiting sense unless otherwise noted.

The terms "a" and "an" and "the" and similar references in the context of describing the invention (especially in the context of the following claims) are to be construed to cover both the singular and the plural, unless otherwise indicated herein or clearly contradicted by context. Where the plural form is used for compounds, salts, and the like, this is taken to mean also a single compound, salt, or the like.

The terms "about" and "approximately" as used herein are used to provide flexibility to a numerical range endpoint by providing that a given value may be "a little above" or "a little below" the endpoint accounting for variations one might see in measurements taken among different instruments, samples, and sample preparations. The term "about" or "approximately" usually means within 10%, more preferably within 5%, and most preferably still within 1% of a given value or range.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

WO2007/084786 describes specific pyrimidine derivative compounds, which have been described to inhibit the activity of phosphatidylinositol 3-kinase (PI3K) and to be useful for the treatment of cancer. The specific pyrimidine derivative compound of formula (I)

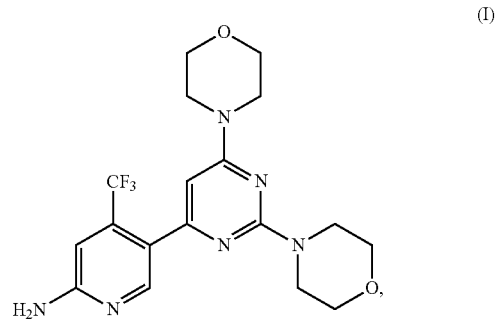 [SMILES: Nc1cc(C(F)(F)F)c(-c2cc(N3CCOCC3)nc(N3CCOCC3)n2)cn1]

(also referred to as or "compound of formula (I)" or "Compound A") and its pharmaceutically acceptable salts are intended for the pharmaceutical compositions of the present invention. The compound of formula (I) has the chemical name 4-(trifluoromethyl)-5-(2,6-dimorpholinopyrimidin-4-yl)pyridin-2-amine. This compound, its pharmaceutically acceptable salts, and its preparation are disclosed in WO2007/084786, which is hereby incorporated by reference in its entirety, e.g., Example 10. Such pyrimidine derivative is proven to be an effective PI3K inhibitor, e.g. WO2007/084786 and S. Maira et al, Molecular Cancer Therapeutics 11:317-328 (2012), that displays broad activity against a large panel of cultured human cancer cell lines.

The compound of formula (I) may be present in the pharmaceutical compositions of the present invention in the form of the free base or a pharmaceutically acceptable salt thereof. Such salts can be prepared in situ during the final isolation and purification of the compound, or by separately reacting the base or acid functions with a suitable organic or inorganic acid or base, respectively. Suitable salts of the compound of formula (I) include but are not limited to the following: acetate, adipate, alginate, citrate, aspartate, benzoate, benzenesulfonate, bisulfate, butyrate, camphorate, camphorsulfonate, digluconate, cyclopentanepropionate, dodecylsulfate, ethanesulfonate, glucoheptanoate, glycerophosphate, hemi-sulfate, heptanoate, hexanoate, fumarate, hydrochloride, hydrobromide, hydroiodide, 2 hydroxyethanesulfonate, lactate, maleate, methanesulfonate, nicotinate, 2 naphth-alenesulfonate, oxalate, pamoate, pectinate, persulfate, 3 phenylproionate, picrate, pivalate, propionate, succinate, sulfate, tartrate, thiocyanate, p toluenesulfonate, and undecanoate. Also, the basic nitrogen-containing groups can be quaternized with such agents as alkyl halides, such as methyl, ethyl, propyl, and butyl chloride, bromides, and iodides; dialkyl sulfates like dimethyl, diethyl, dibutyl, and diamyl sulfates, long chain halides such as decyl, lauryl, myristyl, and stearyl chlorides, bromides and iodides, aralkyl halides like benzyl and phenethyl bromides, and others.

Examples of acids that may be employed to form pharmaceutically acceptable acid addition salts include such inorganic acids as hydrochloric acid, hydroboric acid, nitric acid, sulfuric acid and phosphoric acid and such organic acids as formic acid, acetic acid, trifluoroacetic acid, fumaric acid, tartaric acid, oxalic acid, maleic acid, methanesulfonic acid, succinic acid, malic acid, methanesulfonic acid, benzenesulfonic acid, and p toluenesulfonic acid, citric acid, and acidic amino acids such as aspartic acid and glutamic acid.

Pharmaceutically acceptable salts include, but are not limited to, cations based on the alkali and alkaline earth metals, such as sodium, lithium, potassium, calcium, magnesium, aluminum salts and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine, and the like. Other representative organic amines useful for the formation of base addition salts include diethylamine, ethylenediamine, ethanolamine, diethanolamine, piperazine, pyridine, picoline, triethanolamine and the like, and basic amino acids such as arginine, lysine and ornithine.

A preferred salt form is the hydrochloride salt of the compound of formula (I).

In accordance with the present invention, the compound 4-(trifluoromethyl)-5-(2,6-dimorpholinopyrimidin-4-yl) pyridin-2-amine or a pharmaceutically acceptable salt thereof may be present in the pharmaceutical composition in an amount ranging from about 15% to about 60%, preferably about 20% to about 30% and most preferably about 20% to about 22%, by weight of relative to the total weight of the overall composition. In one embodiment, the compound 4-(trifluoromethyl)-5-(2,6-dimorpholinopyrimidin-4-yl) pyridin-2-amine or a pharmaceutically acceptable salt thereof is present in a therapeutically effective amount that is ranging from between 20 to 22% by weight of relative to the total weight of the overall composition.

In addition to the compound of formula (I) or its pharmaceutically acceptable salt, the solid pharmaceutical compositions of the present invention further comprise the lubricant sodium stearyl fumarate.

It is generally known that lubricants (e.g., magnesium stearate, talc, polyethylene glycol) may be used in the external phase of pharmaceutical compositions to minimize sticking to process equipment. However, it has been discovered that the compound of formula (I) and its pharmaceutically acceptable salts pose significant formulating challenges due to its physiochemical properties. The compound of formula (I) and its pharmaceutically acceptable salts remains sticky and is difficult to handle in a tableting machine even when formulated with most common lubricants, including but not limited to magnesium stearate, talc, and silica.

Sodium stearyl fumarate ($C_{22}H_{39}NaO_4$, CAS Number 4070-80-8) is a lubricant with hydrophilic character that is used in capsule and tablet formulations typically at concentrations of 0.5% to 2.0% w/w. It is commercially available by various suppliers, including under the tradename Pruv® by JRS Pharma LP (Patterson, N.Y., United States).

It has been surprisingly found that use of the specific lubricant sodium stearyl fumarate in formulating the compound 4-(trifluoromethyl)-5-(2,6-dimorpholinopyrimidin-4-yl)pyridin-2-amine or a pharmaceutically acceptable salt thereof by roller compaction significantly improves and/or eliminates the sticking tendency. Further, the resulting pharmaceutical composition has sufficient hardness for a robust product.

Accordingly, the solid pharmaceutical compositions of the present invention comprise (a) the compound 4-(trifluoromethyl)-5-(2,6-dimorpholinopyrimidin-4-yl)pyridin-2-amine or a pharmaceutically acceptable salt thereof, (b) sodium stearyl fumarate, and (c) optionally at least one additional pharmaceutically acceptable carrier and are prepared by roller compaction. These solid pharmaceutical compositions and the embodiments described herein are also referred to as "roller compacted solid pharmaceutical compositions of the present invention" or "pharmaceutical compositions of the present invention".

In accordance with the present invention, the sodium stearyl fumarate is present in the pharmaceutical composition in an amount ranging from about 3% to about 8% by weight relative to the total weight of the overall composition, e.g., about 3% to about 6% by weight relative to the total weight of the overall composition, e.g., about 3% to about 5% by weight relative to the total weight of the overall composition. In a preferred embodiment, the sodium stearyl fumarate is present in the pharmaceutical composition in an amount ranging from 3% to 5% by weight relative to the total weight of the overall composition.

The pharmaceutical compositions of the present invention are prepared by roller compaction. Roller compaction uses an apparatus that essentially utilizes two rollers which roll towards each other. A hydraulic ram forces one of the rollers against the other to exert a compacting force against the ground particles fed into the roller compactor via a screw conveyer system. In accordance with the present invention, the pharmaceutical compositions can be prepared by the method comprising the steps of roller compacting the compound 4-(trifluoromethyl)-5-(2,6-dimorpholinopyrimidin-4-yl)pyridin-2-amine or a pharmaceutically acceptable salt thereof together with sodium stearyl fumarate and optionally at least one additional pharmaceutically acceptable carrier, milling the compacted material to form a plurality of granules, and blending the granules with sodium stearyl fumarate and optionally at least one additional pharmaceutically acceptable carrier, and optionally compressing the final blend into a tablet.

In one embodiment, the pharmaceutical compositions of the present invention can be prepared by the method comprising the steps of:
 (a) blending the compound 4-(trifluoromethyl)-5-(2,6-dimorpholinopyrimidin-4-yl)pyridin-2-amine or a pharmaceutically acceptable salt thereof together with sodium stearyl fumarate and optionally at least one additional pharmaceutically acceptable carrier,
 (b) sieving or screening the blended material,
 (c) roller compacting the sieved or screened material to form a compacted material,
 (d) milling the compacted material to form a plurality of granules,
 (e) blending the granules with sodium stearyl fumarate and optionally at least one additional pharmaceutically acceptable carrier to form a final mixture, and
 (f) optionally compressing the final blend into a tablet.

There are numerous known methods of granulating, sieving and mixing employed in the art, e.g., mixing in a free-fall or tumble blending, compressing into tablets on a single-punch or rotary tablet press or compaction on a roller compaction equipment.

The sieving or screening step can be accomplished using any suitable means, e.g., using oscillating sieving or hand/vibrating sieves or commercially available screening mills fitted with the appropriate size screen. A skilled person in the art will have the experience and knowledge of the how to determine and select the appropriate size screen for the sieving or screening step. For example, the sieving or screening step may be performed using a Quadro-Comil screening mill fitted with the appropriate size screen, e.g. 1.0 mm. Typically, the compound of formula (I) or its pharmaceutically acceptable salts, or its granulate are dispatched to a suitable vessel such as a cylindrical bin blender.

The roller compacting step is accomplished using a roller compactor with a compaction force ranging from about 3600 kPa to about 19,400 kPa, preferably about 4,000 kPa to 6,000 kPa, most preferably about 5,000 kPa, is employed. Preferably the device used is a Vector Corporation roller compactor TFC220. Using this equipment, the screw speed is suitably adjusted to ensure proper quality of the roller compacted material. Preferably, the screw speed is more than about 5 rpm, preferably about 5 rmp to about 35 rpm. Moreover, using this equipment, the roll speed is suitably adjusted to ensure proper quality of the roller compacted material, Preferably, the roll speed is about 2 rpm to about 14 rpm, most preferably about 4 rpm.

The milling/screening step can be accomplished using any suitable means. Typically, the roller compacted material (which forms the "internal phase" of the resulting granules) is milled through a screening mill or oscillating sieve/mill with a screen of at least 1.0 mm mesh size, such as 1.0 or 1.2 mm. Preferably, the roller compacted material is screened using a Quadro-Comil screening mill fitted with a 1.0 mm screen. This milling/screening step produces a plurality of granules.

The blending step of the granules together with sodium stearyl fumarate and optionally at least one additional pharmaceutically acceptable carrier (which forms the "external phase" of the resulting granules) can be accomplished in an cylindrical bin blender. This blending step produces a plurality of granules having an internal phase and an external phase.

The resulting granules may be compressed into a tablet solid dosage form using an appropriate rotary press, including but not limited to a B&D PZ-Uno tablet press preferably with a power assisted punch/die fitted with appropriate tooling at the required target tablet weight. In a preferred embodiment, the rotary press is a B&D PZ-Uno tablet press with a power assisted punch/die fitted with 9 mm round R18 tooling at the required target tablet weight of 250 mg.

Alternatively, the resulting granules may be compressed into solid dosage forms such as pills, lozenges, or caplets or may be filled into solid dosage forms such as capsules or sachets.

Preferably, the resulting granules are compressed into a solid dosage form that is a tablet.

In one embodiment, the present invention provides a roller compacted solid pharmaceutical composition comprising (a) the compound 4-(trifluoromethyl)-5-(2,6-dimorpholinopyrimidin-4-yl)pyridin-2-amine or a pharmaceutically acceptable salt thereof, (b) sodium stearyl fumarate, and (c) optionally at least one additional pharmaceutically acceptable carrier, wherein the pharmaceutical composition contains a plurality of granules having an internal phase and an external phase, and wherein said internal phase and external phase of the granules both include sodium stearyl fumarate.

In one embodiment, the present invention provides a solid dosage form comprising a roller compacted solid pharmaceutical composition comprising (a) the compound 4-(trifluoromethyl)-5-(2,6-dimorpholinopyrimidin-4-yl)pyridin-2-amine or a pharmaceutically acceptable salt thereof, (b) sodium stearyl fumarate, and (c) optionally at least one additional pharmaceutically acceptable carrier. Preferably, the solid dosage form is administered orally. Examples of suitable solid oral dosage forms include but are not limited to tablets, pills, lozenges, caplets, capsules or sachets.

In the preferred embodiment, the solid oral dosage form is a tablet. After the granules are blended with the external phase components, they may be compressed or molded into a monolithic tablet.

Any capsule as known in the art may be used to encapsulate the pharmaceutical composition of the present invention. An example of such capsule is hard gelatin capsules, for example CONI-SNAP manufactured by Capsugel of Morris Plains, N.J. Suitable sizes for such capsules include, but are not limited to size Nos. 00 through 5.

In a preferred embodiment, this invention is directed to the solid oral dosage forms comprising the pharmaceutical composition of the present invention and which are film-coated. Suitable film coatings are known and commercially available or can be made according to known methods. Typically, film coating materials are hydrophilic polymers such as polyethylene glycol, polyvinylpyrrolidone, polyvinyl alcohol, hydroxypropylcellulose, hydroxymethylcellulose, and hydroxypropylmethylcellulose or the like. The film coating composition ingredients may include plasticizers, eg., polyethylene glycols (e.g., polyethylene glycol 6000), triethylcitrate, diethyl phthalate, propylene glycol, glycerin in conventional amounts, as well as opacifiers such as titanium dioxide, and colorants, e.g., iron oxide, aluminum lakes, etc. Typically, a film coating material is applied in such amount as to provide a film coating that ranges from about 1% to about 6% by weight of the total solid oral dosage form. Dry mixtures such as Sepifilm or Opadry mixtures prepared by Colorcon Corp. are preferably used. These products are individually prepared dry pre-mixtures of film forming polymers, opacifiers, colorants and plasticizers which are further processed to aqueous film coating suspensions. Preferably, the film coating is applied to achieve a weight increase of the solid oral dosage form of about 1 to 10% by weight of the total composition, and preferably about 2% to 6% by weight of the total composition.

The film coating may be applied by conventional techniques in a suitable coating pan or fluidized bed apparatus using water and/or conventional organic solvents (e.g, methyl alcohol, ethyl alcohol, isopropyl alcohol), ketones (acetone), etc.

In one embodiment, the present invention provides a roller compacted solid pharmaceutical composition comprising (a) the compound 4-(trifluoromethyl)-5-(2,6-dimorpholinopyrimidin-4-yl)pyridin-2-amine or a pharmaceutically acceptable salt thereof, (b) sodium stearyl fumarate, and (c) optionally at least one additional pharmaceutically acceptable carrier, and wherein said pharmaceutical composition is in the form of a tablet.

In a further embodiment, the present invention provides a roller compacted solid dosage form comprising a solid pharmaceutical composition comprising (a) the compound 4-(trifluoromethyl)-5-(2,6-dimorpholinopyrimidin-4-yl)

pyridin-2-amine or a pharmaceutically acceptable salt thereof, (b) sodium stearyl fumarate, and (c) optionally at least one additional pharmaceutically acceptable carrier. Preferably, the solid dosage form is a tablet.

In a further embodiment, the present invention provides a film-coated tablet comprising a roller compacted solid pharmaceutical composition comprising (a) the compound 4-(trifluoromethyl)-5-(2,6-dimorpholinopyrimidin-4-yl)pyridin-2-amine or a pharmaceutically acceptable salt thereof, (b) sodium stearyl fumarate, and (c) optionally at least one additional pharmaceutically acceptable carrier. Preferably, the film-coated tablets having a suitable hardness (e.g, an average hardness ranging from about 50N to about 160N, preferably about 70 N to about 110 N). Such an average hardness is determined after the application of any film coating on the tablet.

In a further embodiment, the pharmaceutical compositions of the present invention can be prepared by the method comprising the steps of roller compacting the compound 4-(trifluoromethyl)-5-(2,6-dimorpholinopyrimidin-4-yl) pyridin-2-amine or a pharmaceutically acceptable salt thereof together with sodium stearyl fumarate and optionally at least one additional pharmaceutically acceptable carrier, milling the compacted material to form a plurality of granules, and blending the granules with sodium stearyl fumarate and optionally at least one additional pharmaceutically acceptable carrier, compressing the final blend into a tablet, and applying a film-coating to the tablet.

In a further embodiment, the pharmaceutical compositions of the present invention can be prepared by the method comprising the steps of:
(a) blending the compound 4-(trifluoromethyl)-5-(2,6-dimorpholinopyrimidin-4-yl)pyridin-2-amine or a pharmaceutically acceptable salt thereof together with sodium stearyl fumarate and optionally at least one additional pharmaceutically acceptable carrier,
(b) sieving or screening the blended material,
(c) roller compacting the sieved or screened material to form a compacted material,
(d) milling the compacted material to form a plurality of granules,
(e) blending the granules with sodium stearyl fumarate and optionally at least one additional pharmaceutically acceptable carrier to form a final mixture, and
(f) compressing the final blend into a tablet, and
(g) applying a film-coat to the tablet.

The pharmaceutical compositions of the present invention may optionally further comprise at least one additional pharmaceutically acceptable carrier used for pharmaceuticals. Examples of such carriers include, but are not limited to, diluents and fillers, disintegrants, glidants, binders, stabilizers, colorants, flavours and preservatives. One of ordinary skill in the art may select one or more of the aforementioned excipients with respect to the particular desired properties of the solid pharmaceutical composition by routine experimentation and without any undue burden. The amount of each carrier used may vary within ranges conventional in the art. The following references which are all hereby incorporated by reference disclose techniques and excipients used to formulate oral dosage forms. See The Handbook of Pharmaceutical Excipients, 4th edition, Rowe et al., Eds., American Pharmaceuticals Association (2003); and Remington: the Science and Practice of Pharmacy, 20th edition, Gennaro, Ed., Lippincott Williams & Wilkins (2003).

Examples of pharmaceutically acceptable fillers and pharmaceutically acceptable diluents include, but are not limited to, microcrystalline cellulose, mannitol, confectioner's sugar, compressible sugar, dextrates, dextrin, dextrose, lactose, powdered cellulose, sorbitol, sucrose and talc or combinations thereof. Preferably, the diluents are microcrystalline cellulose and/or mannitol. The filler and/or diluent, e.g., may be present in an amount from about 20 to about 80%, preferably about 40% to about 70%, by weight based upon the total weight of the composition.

Examples of pharmaceutically acceptable disintegrants include, but are not limited to, starches; celluloses; alginates; gums; cross-linked polymers, e.g., cross-linked polyvinyl pyrrolidone or crospovidone (e.g. POLYPLASDONE XL from International Specialty Products (Wayne, N.J.)); cross-linked sodium carboxymethylcellulose or croscarmellose sodium (e.g., AC-DI-SOL from FMC); cross-linked calcium carboxymethylcellulose; soy polysaccharides; sodium starch glycolate; and guar gum or combinations thereof. Preferably, the disintegrant is crospovidone. The disintegrant may be present in an amount from about 1% to about 15%, preferably about 2% to about 10%, by weight based upon the total weight of the composition.

Examples of pharmaceutically acceptable binders include, but are not limited to, starches; celluloses and derivatives thereof, for example, microcrystalline cellulose, e.g., AVICEL PH from FMC (Philadelphia, Pa.), hydroxypropyl cellulose hydroxylethyl cellulose and hydroxylpropylmethyl cellulose METHOCEL from Dow Chemical Corp. (Midland, Mich.); sucrose; dextrose; corn syrup; polysaccharides; and gelatin, or a combination thereof. The binder may be present in an amount from about 0.01% to about 10% by weight based on the total weight of the composition.

Examples of pharmaceutically acceptable glidants include, but are not limited to, colloidal silicon dioxide (e.g, Aerosol 200), magnesium trisilicate, powdered cellulose, talc and combiantions thereof. Preferably, the glidant is colloidal silicon dioxide (e.g, Aerosol 200). The glidant may be present in an amount from about 0.1% to about 10%, preferably from 0.1% to 4%, by weight based on the total weight of the composition.

In one embodiment, the pharmaceutical composition of the present invention comprises at least one additional pharmaceutically acceptable carrier selected from a diluent, a disintegrant, a glidant, or a combination thereof.

In one embodiment, the pharmaceutical composition of the present invention comprises at least one additional pharmaceutically acceptable carrier selected from a diluent present in an amount from about 40% to about 70% by weight of the composition, a disintegrant present in an amount from about 2% to about 15% by weight of the composition, a glidant present in an amount from about 0.1% to about 4% by weight of the composition, or a combination thereof.

In a further embodiment, the roller compacted solid pharmaceutical composition of the present invention comprises comprising (a) the compound 4-(trifluoromethyl)-5-(2,6-dimorpholinopyrimidin-4-yl)pyridin-2-amine or a pharmaceutically acceptable salt thereof, (b) sodium stearyl fumarate, (c) microcrystalline cellulose, (d) crospovidone, and (e) colloidal silicon dioxide. Preferably, this roller compacted solid pharmaceutical composition is capable of an in vitro dissolution of the compound 4-(trifluoromethyl)-5-(2,6-dimorpholinopyrimidin-4-yl)pyridin-2-amine or a pharmaceutically acceptable salt thereof of 90% or more in 15 minutes or less.

In a further embodiment, the roller compacted solid pharmaceutical composition of the present invention comprises comprising (a) the compound 4-(trifluoromethyl)-5-(2,6-dimorpholinopyrimidin-4-yl)pyridin-2-amine or a pharmaceutically acceptable salt thereof, (b) sodium stearyl fumarate, (c) microcrystalline cellulose, (d) mannitol, (e) crospovidone, and (f) colloidal silicon dioxide. Preferably, this solid pharmaceutical composition is capable of an in vitro dissolution of the compound 4-(trifluoromethyl)-5-(2,6-dimorpholinopyrimidin-4-yl)pyridin-2-amine or a pharmaceutically acceptable salt thereof of 90% or more in 30 minutes or less.

In one embodiment, the present invention is related to a process for the manufacture of a solid pharmaceutical composition comprising the steps of roller compacting the compound 4-(trifluoromethyl)-5-(2,6-dimorpholinopyrimidin-4-yl)pyridin-2-amine or a pharmaceutically acceptable salt thereof together with sodium stearyl fumarate and optionally at least one additional pharmaceutically acceptable carrier, milling the compacted material to form a plurality of granules, and blending the granules with sodium stearyl fumarate and optionally at least one additional pharmaceutically acceptable carrier, and optionally compressing the final blend into a tablet.

In a further embodiment, the present invention is related to a process for the manufacture of a solid pharmaceutical composition comprising the steps of:
(a) blending the compound 4-(trifluoromethyl)-5-(2,6-dimorpholinopyrimidin-4-yl)pyridin-2-amine or a pharmaceutically acceptable salt thereof together with sodium stearyl fumarate and optionally at least one additional pharmaceutically acceptable carrier,
(b) sieving or screening the blended material,
(c) roller compacting the sieved or screened material to form a compacted material,
(d) milling the compacted material to form a plurality of granules,
(e) blending the granules with sodium stearyl fumarate and optionally at least one additional pharmaceutically acceptable carrier to form a final mixture, and
(f) optionally compressing the final blend into a tablet.

In one embodiment, the present invention is related to a process for the manufacture of a film-coated tablet comprising the steps of roller compacting the compound 4-(trifluoromethyl)-5-(2,6-dimorpholinopyrimidin-4-yl)pyridin-2-amine or a pharmaceutically acceptable salt thereof together with sodium stearyl fumarate and optionally at least one additional pharmaceutically acceptable carrier, milling the compacted material to form a plurality of granules, and blending the granules with sodium stearyl fumarate and optionally at least one additional pharmaceutically acceptable carrier, compressing the final blend into a tablet, and optionally applying a film-coat to the tablet.

In a further embodiment, the present invention is related to a process for the manufacture of a film-coated tablet comprising the steps of:
(a) blending the compound 4-(trifluoromethyl)-5-(2,6-dimorpholinopyrimidin-4-yl)pyridin-2-amine or a pharmaceutically acceptable salt thereof together with sodium stearyl fumarate and optionally at least one additional pharmaceutically acceptable carrier,
(b) sieving or screening the blended material,
(c) roller compacting the sieved or screened material to form a compacted material,
(d) milling the compacted material to form a plurality of granules,
(e) blending the granules with sodium stearyl fumarate and optionally at least one additional pharmaceutically acceptable carrier to form a final mixture, and
(f) compressing the final blend into a tablet, and
(g) applying a film-coat to the tablet.

The resulting pharmaceutical compositions of the present invention show the following advantages:
The poor flowability and sticking tendency is significantly improved and/or eliminated.
The formulation of solid dosage forms with sufficient hardness.
The formulation of pharmaceutical compositions with a fast dissolution rate. Specifically, the solid pharmaceutical compositions of the present invention are capable of an in vitro dissolution of the compound 4-(trifluoromethyl)-5-(2,6-dimorpholinopyrimidin-4-yl)pyridin-2-amine or a pharmaceutically acceptable salt thereof of 90% or more in 30 minutes or less.
A robust manufacturing process is achieved.
Scale-up formulation and process resulting in reproducible performance is achieved.

The pharmaceutical compositions of the present invention and solid dosage forms thereof are useful for the treatment of cancer, particularly cancer diseases that can be beneficially treated by the inhibition of PI3K. Examples of cancer suitable for treatment with the solid pharmaceutical compositions of the present invention include, but are not limited to, for example, lung cancer (including small cell lung cancer and non-small cell lung cancer), breast cancer, prostate cancer, pancreatic cancer, colon and rectum cancer, thyroid cancer, liver and intrahepatic bile duct cancer, hepatocellular cancer, gastric cancer, glioma/glioblastoma, endometrial cancer, melanoma, kidney and renal pelvic cancer, urinary bladder cancer, uterine corpus cancer, uterine cervix cancer, ovarian cancer, multiple myeloma, esophageal cancer, neuroendocrine tumor, leukemia, lymphoma, brain cancer, head and neck cancer, small intestinal cancer, melanoma, and villous colon adenoma. Additional diseases which may be treated with the solid pharmaceutical composition of the present invention are disclosed in WO2007/084786, which is hereby incorporated by reference in its entirety.

Preferably, the cancer is selected from the group consisting of lung cancer (including small cell lung cancer and non-small cell lung cancer), breast cancer, prostate cancer, pancreatic cancer, colon and rectum cancer, glioma/glioblastoma, neuroendocrine tumor, head and neck cancer, and endometrial cancer.

Ultimately, the exact dose of the therapeutic compound of formula (I) and the particular pharmaceutical composition to be administered depends on a number of factors, e.g., type, species, age, weight, sex and medical condition of the patient, the condition to be treated, the severity of the condition to be treated, the route of administration, the renal and hepatic function of the patient, the desired duration of the treatment and the rate of release of the therapeutic compound. For example, the amount of therapeutic agent required and the release rate may be determined on the basis of known in vitro or in vivo techniques, determining how long a particular therapeutic agent concentration in the blood plasma remains at an acceptable level for a therapeutic effect. The utility of all the pharmaceutical compositions of the present invention and solid dosage forms thereof may be observed in standard clinical test, for example, known indications of drug dosages giving therapeutically effective blood levels of the therapeutic compound. A physician, clinician or veterinarian of ordinary skill can readily determine and prescribe the effective amount of the compound of formula (I) or its pharmaceutically acceptable salt thereof required to treat, prevent, counter or arrest the progress of a condition. Optimal precision in achieving concentration of the compound of formula (I) or its pharmaceutically acceptable salt thereof within the range that yields efficacy requires a regimen based on the kinetics of the drug's availability to target sites. This involves a consideration of the distribution, equilibrium, and elimination of the compound of formula (I) or its pharmaceutically acceptable salt thereof.

Using a total daily dose administered to a host in single or divided doses in amounts, the compound of formula (I) or its pharmaceutically acceptable salt thereof may be administered at a dosage of from about 0.001 to 1000 mg/kg body weight daily and more preferred from 1.0 to 30 mg/kg body weight daily. Treatment regimens according to the present invention may comprise administration of the compound of formula (I) or a pharmaceutically acceptable salt thereof to a patient in need of such treatment from about 10 mg to about 2000 mg, preferably from about 50 mg to about 200 mg or more preferably from about 60 mg to about 120 mg or most preferably about 100 mg per day, of the compound of formula (I) or a pharmaceutically acceptable salt thereof per day in single or multiple doses.

For purposes of the present invention, the compound of formula (I) or a pharmaceutically acceptable salt thereof may be administered at a therapeutically effective dosage of about 60 to about 120 mg per day to a human patient in need thereof. The total daily dose may be administered to the human patient in single or divided doses. The pharmaceutical compositions of the present invention may be formulated into solid dosage form units that contain such amounts of submultiples thereof to make up the daily dose. In general, treatment regimens according to the present invention comprise administration to a patient in need of such treatment from about 60 mg to about 120 mg of the compound(s) of this invention per day in single or multiple doses. In accordance with the present invention, the compound of formula (I) is administered to a human patient in need thereof at a dosage of about 60 to about 120 mg daily for each day of the week or for five consecutive days in any seven day period. In the preferred embodiment, the compound of formula (I) or a pharmaceutically acceptable salt thereof is administered at dosage of about 100 mg daily for each day of the week or for five consecutive days in any seven day period.

In one embodiment, the present invention provides the roller compacted solid pharmaceutical composition of the present invention for use for the treatment of cancer.

In one embodiment, the present invention provides the use of a roller compacted solid pharmaceutical composition of the present invention for the manufacture of a medicament for the treatment of cancer.

In one embodiment, the present invention provides a method for the treatment of cancer comprising administering a roller compacted solid composition of the present invention comprising a therapeutically effective amount of the compound of formula (I) or a pharmaceutically acceptable salt thereof to a patient suffering from such cancer.

In further aspects, the present invention further provides:

A roller compacted solid pharmaceutical composition comprising (a) the compound 4-(trifluoromethyl)-5-(2,6-dimorpholinopyrimidin-4-yl)pyridin-2-amine or a pharmaceutically acceptable salt thereof, (b) sodium stearyl fumarate, in an amount ranging from about 3% to about 8% by weight relative to the total weight of the overall composition and (c) optionally at least one additional pharmaceutically acceptable carrier.

A roller compacted solid pharmaceutical composition comprising (a) the compound 4-(trifluoromethyl)-5-(2,6-dimorpholinopyrimidin-4-yl)pyridin-2-amine or a pharmaceutically acceptable salt thereof in an amount ranging from about 20% to about 22% by weight relative to the total weight of the overall composition, (b) sodium stearyl fumarate, in an amount ranging from about 3% to about 8% by weight relative to the total weight of the overall composition and (c) optionally at least one additional pharmaceutically acceptable carrier.

It is understood that the solid pharmaceutical composition of the present invention refers to any individual embodiment described herein.

The details of one or more embodiments of the disclosure are set forth in the accompanying description above. Although any methods and materials similar or equivalent to those described herein can be used in the practice or testing of the present disclosure, the preferred methods and materials are now described. Other features, objects, and advantages of the disclosure will be apparent from the description and from the claims. In the specification and the appended claims, the singular forms include plural referents unless the context clearly dictates otherwise. Unless defined otherwise, all technical and scientific terms used herein have the same meaning as commonly understood by one of ordinary skill in the art to which this disclosure belongs. All patents and publications cited in this specification are incorporated by reference. The following Examples are presented in order to more fully illustrate the preferred embodiments of the disclosure. These examples should in no way be construed as limiting the scope of the disclosed patient matter, as defined by the appended claims.

EXAMPLES

Example 1

Tablet Formulation and Process Parameters

Compositions of Compound A 50 mg (Free Base) Coated Tablets.

| Tablet Core: | Dosage Form 1 | |
|---|---|---|
| | Mg/unit | Composition per unit (%) |
| Intragranular portion | | |
| Compound A hydrochloride salt[1] | 54.45 | 20.94 |
| Microcrystalline cellulose (Avicel PH102)[2] | 126.80 | 48.77 |
| Crospovidone PVPP XL | 10.00 | 3.85 |
| Sodium Stearyl Fumarate | 3.13 | 1.20 |
| Colloidal silicon dioxide/ Silica, colloidal anhydrous (Aerosil 200PH) | 2.50 | 0.96 |
| Extragranular portion | | |
| Microcrystalline cellulose (Avicel PH102) | 35.00 | 13.46 |
| Sodium Stearyl Fumarate | 9.38 | 3.61 |
| Crospovidone PVPP XL | 7.50 | 2.88 |
| Colloidal silicon dioxide/ Silica, colloidal anhydrous (Aerosil 200PH) | 1.25 | 0.48 |
| Core tablet weight | 250.00 | |

-continued

| Tablet Core: | Mg/unit | Composition per unit (%) |
|---|---|---|
| Coating | | |
| Basic coating premix, white | 8.12 | 3.12 |
| Basic coating premix, yellow | 1.57 | 0.60 |
| Basic coating premix, red | 0.29 | 0.11 |
| Basic coating premix, black | 0.026 | 0.01 |
| Water, purified[3] | — | |
| Coated tablet weight | 260.00 | |

[1]1.089 mg of Compound A salt is equivalent to 1.000 mg of Compound A base
[2]Drug substance quantity is adjusted for drug content <99.5 with microcrystalline cellulose
[3]Removed during processing Preparation The composition is prepared by weighing the Compound A hydrochloride salt and the excipients.

The intragranular portion is prepared by dry blending microcrystalline cellulose (one-third of total amount for the intragranular portion), Compound A hydrochloride salt, crospovidone PVPP XL, colloidal silicon dioxide/silica colloidal anhydrous (Aerosil 200PH), sodium stearyl fumarate and microcrystalline cellulose (two-third of total amount for the intragranular portion) for approximately 15 minutes using a cylindrical bin blender (rotation speed 15 rpm). The mixture is screened using a Quadro-Comil screening mill fitted with a 1.0 mm screen, round (rotation speed 200 rpm). The mixture is dry blended again for approximately 15 minutes using a cylindrical bin blender (rotation speed 15 rpm). The mixture is discharged and compacted using a Vector roller compactor TFC220 with the following process parameters:

| Roller compaction parameters | |
|---|---|
| Compaction force (kPa) | 5000 |
| Roller speed (rpm) | 4 rpm |
| Gap width | Approximately 2.0 mm |

The compacted ribbons are milled using a Quadro-Comil screening mill fitted with a 0.8 mm conidur screen (500 rpm).

The extragranular portion is prepared by screening the blending microcrystalline cellulose, sodium stearyl fumarate, crospovidone PVPP XL, and colloidal silicon dioxide/silica colloidal anhydrous (Aerosil 200PH) using a Quadro-Comil screening mill fitted with a 1.0 mm screen, round (rotation speed 200 rpm). The sieved excipients are added directly to the milled granules and dry blended for approximately 15 minutes using a cylindrical bin blender (rotation speed 15 rpm). The final blend is compressed using a B&D PZ-Uno tablet press with power assisted punch/die fitted with 9 mm round biconvex R18 tooling at the required target tablet weight of 250 mg.

The coating premixes (e.g, Opadry) are mixed with purified water and dispersed to form a coating suspension. The uncoated tablets are de-dusted and subsequently coated with the coating suspension using a Nicomac Lab30 non-perforated pan-coating system (air-flow rate: 200-500 m$^3$/hour, inlet air temperature of spraying phase: 60-70° C. and of cooling phase 20-30° C., spray rate: 15-70 g/min, spray pressure 1.5-2.2 bar with 2 1.2 mm diameter nozzles, rotation speed of coating pan: 1-10 rmp). The uncoated tablets are coated until a target weight gain of approximately 4% as compared to uncoated tablet.

The in-process controls are as follows (target values):

| Control | Range |
|---|---|
| Shape | Round curved, 9.1-9.2 mm diameter |
| Tablet thickness | 3.45-3.85 mm |
| Hardness | 90N |
| Disintegration time (with disk): 6 units, purified water, 37° C. ± 2° C. | ≤20 minutes |

Dissolution

The dissolution rate of the solid pharmaceutical composition of Example 1 is measured by conventional dissolution methods (single pH). The single stage conventional dissolution method (in pH 2, Hydrochloric acid 0.01 N) is used. For Paddle Method According to USP <711> at pH 2:

The assembly consists of the following: a covered vessel made of glass or other inert, transparent material; a motor, and a paddle formed from a blade and shaft as the stirring element. The vessel is partially immersed in a suitable water bath of any convenient size or placed in a heating jacket. The water bath or heating jacket permits holding the temperature inside the vessels at 37±0.5° during the test and keeping the bath fluid in constant, smooth motion. No part of the assembly, including the environment in which the assembly is placed, contributes significant motion, agitation, or vibration beyond that due to the smoothly rotating stirring element. Apparatus that permits observation of the specimen and stirring element during the test is has the following dimensions and capacities: the height is 160 mm to 210 mm and its inside diameter is 98 mm to 106 mm. Its sides are flanged at the top. A fitted cover may be used to retard evaporation.

The shaft is positioned so that its axis is not more than 2 mm at any point from the vertical axis of the vessel and rotates smoothly without significant wobble. The vertical center line of the blade passes through the axis of the shaft so that the bottom of the blade is flush with the bottom of the shaft. The distance of 25±2 mm between the blade and the inside bottom of the vessel is maintained during the test. The metallic or suitably inert, rigid blade and shaft comprise a single entity. A suitable two-part detachable design may be used provided the assembly remains firmly engaged during the test. The paddle blade and shaft may be coated with a suitable inert coating. The dosage unit is allowed to sink to the bottom of the vessel before rotation of the blade is started. A small, loose piece of nonreactive material such as not more than a few turns of wire helix may be attached to dosage units that would otherwise float. Other validated sinker devices may be used.

900 mL of the dissolution medium (Hydrochloric acid 0.01N, pH 2.0) is placed in the vessel of the apparatus, the apparatus is assembled, the dissolution medium is equilibrated to 37±0.5° C. Dosage form (e.g. tablet) is placed on the apparatus, and immediately the apparatus is operated at a rate of 50±2 rpm. At the time interval specified, a specimen (≥1 ml) is withdrawn The specimen is filtered through a suitable filter, e.g. a 0.45 mm PVDF filter. The analysis is performed by HPLC or UV detection.

Figure 4:
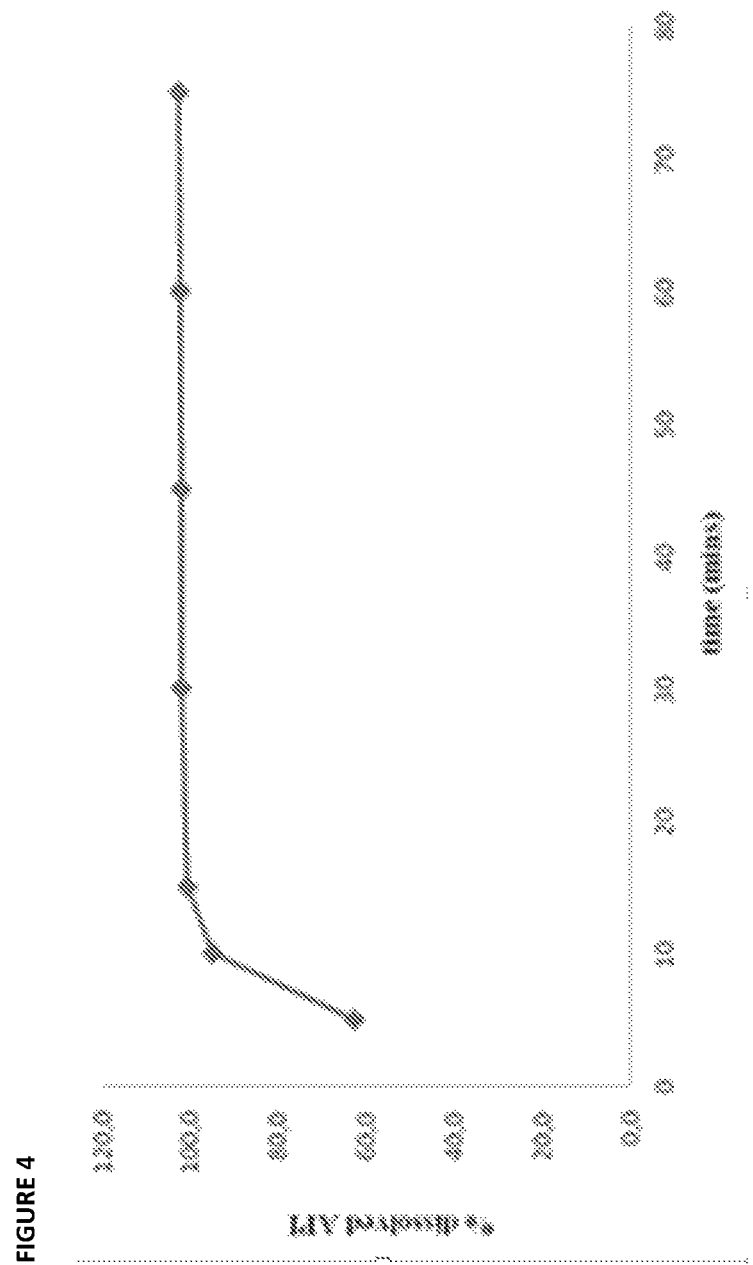
FIG. 4 shows the dissolution rate measured for the pharmaceutical composition of Example 1.

Following this procedure, the solid pharmaceutical composition of Example 1 shows an in vitro dissolution of the compound 4-(trifluoromethyl)-5-(2,6-dimorpholinopyrimidin-4-yl)pyridin-2-amine or a pharmaceutically acceptable salt thereof of 90% or more in 10 minutes or less. The results are shown in FIG. 4 herein.

Example 2

Tablet Formulation and Process Parameters

Compositions of Compound A 50 mg (Free Base) Uncoated Tablets.

| Tablet Core: | Dosage Form 2 | |
|---|---|---|
| | Mg/unit | Composition per unit (%) |
| Intragranular portion | | |
| Compound A hydrochloride salt[1] | 54.45 | 21.78 |
| Microcrystalline cellulose (Avicel PH102)[2] | 126.80 | 50.72 |
| Crospovidone PVPP XL | 10.00 | 4.00 |
| Sodium Stearyl Fumarate | 3.13 | 1.25 |
| Colloidal silicon dioxide/ Silica, colloidal anhydrous (Aerosil 200PH) | 2.50 | 1.00 |
| Extragranular portion | | |
| Microcrystalline cellulose (Avicel PH102) | 35.00 | 14.00 |
| Sodium Stearyl Fumarate | 9.38 | 3.75 |
| Crospovidone PVPP XL | 7.50 | 3.00 |
| Colloidal silicon dioxide/ Silica, colloidal anhydrous (Aerosil 200PH) | 1.25 | 0.5 |
| Core tablet weight | 250.00 | |

[1]1.089 mg of Compound A salt is equivalent to 1.000 mg of Compound A base
[2]Drug substance quantity is adjusted for drug content <99.5 with microcrystalline
[3]Removed during processing Preparation The composition is prepared by weighing the Compound A hydrochloride salt and the excipients.

The intragranular portion is prepared by dry blending microcrystalline cellulose (one-third of total amount for the intragranular portion), Compound A hydrochloride salt, crospovidone PVPP XL, colloidal silicon dioxide/Silica colloidal anhydrous (Aerosil 200PH), sodium stearyl fumarate and microcrystalline cellulose (two-third of total amount for the intragranular portion) for approximately 15 minutes using a cylindrical bin blender (rotation speed 15 rpm). The mixture is screened using a Quadro-Comil screening mill fitted with a 1.0 mm screen, round (rotation speed 200 rpm). The mixture is dry blended again for approximately 15 minutes using a cylindrical bin blender (rotation speed 15 rpm). The mixture is discharged and compacted using a Vector roller compactor TFC220 with the following process parameters:

| Roller compaction parameters | |
|---|---|
| Compaction force (kPa) | 5000 |
| Roller speed (rpm) | 4 rpm |
| Gap width | Approximately 2.0 mm |

The compacted ribbons are milled using a Quadro-Comil screening mill fitted with a 0.8 mm conidur screen (500 rpm).

The extragranular portion is prepared by screening the blending microcrystalline cellulose, sodium stearyl fumarate, crospovidone PVPP XL, and colloidal silicon dioxide/ silica colloidal anhydrous (Aerosil 200PH) using a Quadro-Comil screening mill fitted with a 1.0 mm screen, round (rotation speed 200 rpm). The sieved excipients are added directly to the milled granules and dry blended for approximately 15 minutes using a cylindrical bin blender (rotation speed 15 rpm). The final blend is compressed using a B&D PZ-Uno tablet press with power assisted punch/die fitted with 9 mm round biconvex R18 tooling at the required target tablet weight of 250 mg.

Figure 2:
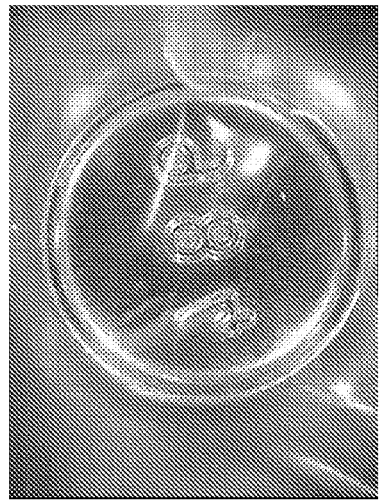
FIG. 2 shows photographic images displaying the minimal to lack of sticking and picking of the solid pharmaceutical composition of Example 2.
Figure 2:
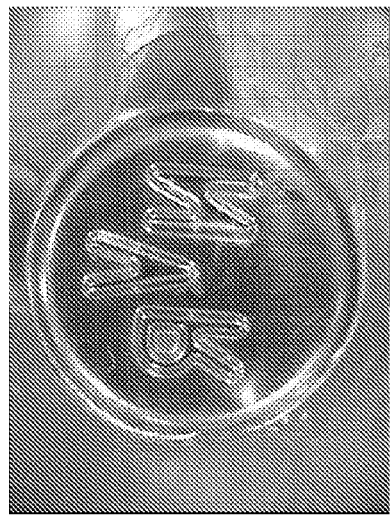

FIG. 2 provides photographic images displaying the minimal to lack of sticking and picking to the tablet punch of the solid pharmaceutical composition of this Example. This is a significant improvement as compared to the sticking and picking to the tablet punch of a previous direct compression pharmaceutical composition comprising the compound of formula (I) hydrochloride salt and the lubricant magnesium stearate vegetable (2% by weight relative to the weight of the overall composition), as shown in FIG. 1.

Example 3

Tablet Formulation and Process Parameters

Compositions of Compound A 50 mg (Free Base) Tablets.

| Tablet Core: | Dosage Form 3 | |
|---|---|---|
| | Mg/unit | Composition per unit (%) |
| Intragranular portion | | |
| Compound A hydrochloride salt[1] | 54.45 | 20.94 |
| Microcrystalline cellulose (Avicel PH102)[2] | 104.3 | 40.12 |
| Mannitol | 25.50 | 9.81 |
| Crospovidone PVPP XL | 7.50 | 2.88 |
| Sodium Stearyl Fumarate | 2.50 | 0.96 |
| Colloidal silicon dioxide/ Silica, colloidal anhydrous (Aerosil 200PH) | 2.50 | 0.96 |
| Extragranular portion | | |
| Microcrystalline cellulose (Avicel PH102) | 37.00 | 14.23 |
| Sodium Stearyl Fumarate | 10.00 | 3.85 |
| Crospovidone PVPP XL | 5.00 | 1.92 |
| Colloidal silicon dioxide/ Silica, colloidal anhydrous (Aerosil 200PH) | 1.25 | 0.48 |
| Core tablet weight | 250.00 | |
| Coating | | |
| Basic lack white | 8.12 | 3.12 |
| Basic lack yellow | 1.57 | 0.60 |
| Basic lack red | 0.29 | 0.11 |
| Basic lack black | 0.026 | 0.01 |
| Water, purified[3] | — | |
| Coated tablet weight | 260.00 | |

[1]1.089 mg of Compound A salt is equivalent to 1.000 mg of Compound A base
[2]Drug substance quantity is adjusted for drug content ≤99.5% with microcrystalline cellulose from the inner phase.
[3]Removed during processing Preparation The composition is prepared by weighing the Compound A hydrochloride salt and the excipients.

The intragranular portion is prepared by dry blending microcrystalline cellulose (one-third of total amount for the intragranular portion), Compound A hydrochloride salt, mannitol, crospovidone PVPP XL, colloidal silicon dioxide/ silica colloidal anhydrous (Aerosil 200PH), sodium stearyl fumarate and microcrystalline cellulose (two-third of total amount for the intragranular portion) for approximately 15 minutes using a cylindrical bin blender (rotation speed 15 rpm). The mixture is screened using a Quadro-Comil screening mill fitted with a 1.0 mm screen, round (rotation speed 200 rpm). The mixture is dry blended again for approximately 15 minutes using a cylindrical bin blender (rotation speed 15 rpm). The mixture is discharged and compacted using a Vector roller compactor TFC220 with the following process parameters:

| Roller compaction parameters | |
|---|---|
| Compaction force (kPa) | 5000 |
| Roller speed (rpm) | 4 rpm |
| Gap width | Approximately 2.0 mm |

The compacted ribbons are milled using a Quadro-Comil screening mill fitted with a 0.8 mm conidur screen (500 rpm).

The extragranular portion is prepared by screening the blending microcrystalline cellulose, sodium stearyl fumarate, crospovidone PVPP XL, and colloidal silicon dioxide/ silica colloidal anhydrous (Aerosil 200PH) using a Quadro-Comil screening mill fitted with a 1.0 mm screen, round (rotation speed 200 rpm). The sieved excipients are added directly to the milled granules and dry blended for approximately 15 minutes using a cylindrical bin blender (rotation speed 15 rpm). The final blend is compressed using a B&D PZ-Uno tablet press with power assisted punch/die fitted with 9 mm round biconvex R18 tooling at the required target tablet weight of 250 mg.

The coating premixes (e.g, Opadry) are mixed with purified water and dispersed to form a coating suspension. The uncoated tablets are de-dusted and subsequently coated with the coating suspension using a Nicomac Lab30 non-perforated pan-coating system (air-flow rate: 200-500 m³/hour, inlet air temperature of spraying phase: 60-70° C. and of cooling phase 20-30° C., spray rate: 15-70 g/min, spray pressure 1.5-2.2 bar with 2 1.2 mm diameter nozzles, rotation speed of coating pan: 1-10 rmp). The uncoated tablets are coated until a target weight gain of approximately 4% as compared to uncoated tablet.

The in-process controls are as follows (target values):

| Control | Range |
|---|---|
| Shape | Round curved, 9.1-9.2 mm diameter |
| Tablet thickness | 3.45-3.85 mm |
| Hardness | 90N |
| Disintegration time (with disk): 6 units, purified water, 37° C. ± 2° C. | ≤30 minutes |

Dissolution

Figure 5:
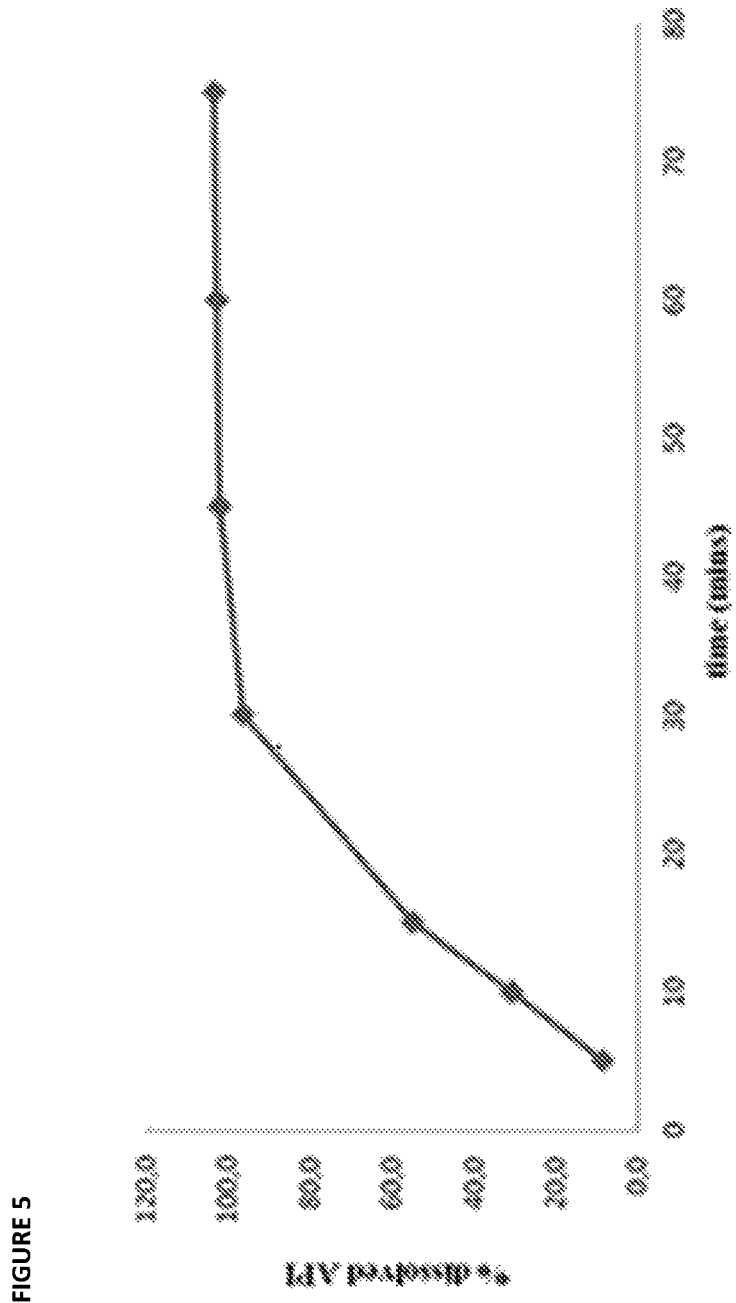
FIG. 5 shows the dissolution rate measured for the pharmaceutical composition of Example 3.

Following the dissolution procedure described in Example 1 above, the solid pharmaceutical composition of Example 3 shows an in vitro dissolution of the compound 4-(trifluoromethyl)-5-(2,6-dimorpholinopyrimidin-4-yl) pyridin-2-amine or a pharmaceutically acceptable salt thereof of 90% or more in 30 minutes or less. The results are shown in FIG. 5 herein.

Example 4

Tablet Formulation and Process Parameters

Compositions of Compound A 50 mg (Free Base) Uncoated Tablets.

| Tablet Core: | Dosage Form 4 | |
|---|---|---|
| | Mg/unit | Composition per unit (%) |
| Intragranular portion | | |
| Compound A hydrochloride salt[1] | 54.45 | 21.78 |
| Microcrystalline cellulose (Avicel PH102)[2] | 104.30 | 41.72 |
| Mannitol | 25.50 | 10.2 |
| Crospovidone PVPP XL | 7.50 | 3.00 |
| Sodium Stearyl Fumarate | 2.50 | 1.00 |
| Colloidal silicon dioxide/ Silica, colloidal anhydrous (Aerosil 200PH) | 2.50 | 1.00 |
| Extragranular portion | | |
| Microcrystalline cellulose (Avicel PH102) | 37.00 | 14.80 |
| Sodium Stearyl Fumarate | 10.00 | 4.00 |
| Crospovidone PVPP XL | 5.00 | 2.00 |
| Colloidal silicon dioxide/ Silica, colloidal anhydrous (Aerosil 200PH) | 1.25 | 0.5 |
| Core tablet weight | 250.00 | |

[1]1.089 mg of Compound A salt is equivalent to 1.000 mg of Compound A base
[2]Drug substance quantity is adjusted for drug content ≤99.5% with microcrystalline cellulose from the inner phase.
[3]Removed during processing Preparation The composition is prepared by weighing the Compound A hydrochloride salt and the excipients.

The intragranular portion is prepared by dry blending microcrystalline cellulose (one-third of total amount for the intragranular portion), Compound A hydrochloride salt, mannitol, crospovidone PVPP XL, colloidal silicon dioxide/ silica colloidal anhydrous (Aerosil 200PH), sodium stearyl fumarate and microcrystalline cellulose (two-third of total amount for the intragranular portion) for approximately 15 minutes using a cylindrical bin blender (rotation speed 15 rpm). The mixture is screened using a Quadro-Comil screening mill fitted with a 1.0 mm screen, round (rotation speed 200 rpm). The mixture is dry blended again for approximately 15 minutes using a cylindrical bin blender (rotation speed 15 rpm). The mixture is discharged and compacted using a Vector roller compactor TFC220 with the following process parameters:

| Roller compaction parameters | |
|---|---|
| Compaction force (kPa) | 5000 |
| Roller speed (rpm) | 4 rpm |
| Gap width | Approximately 2.0 mm |

The compacted ribbons are milled using a Quadro-Comil screening mill fitted with a 0.8 mm conidur screen (500 rpm).

The extragranular portion is prepared by screening the blending microcrystalline cellulose, sodium stearyl fumarate, crospovidone PVPP XL, and colloidal silicon dioxide/ silica colloidal anhydrous (Aerosil 200PH) using a Quadro-Comil screening mill fitted with a 1.0 mm screen, round (rotation speed 200 rpm). The sieved excipients are added directly to the milled granules and dry blended for approximately 15 minutes using a cylindrical bin blender (rotation speed 15 rpm). The final blend is compressed using a B&D PZ-Uno tablet press with power assisted punch/die fitted with 9 mm round biconvex R18 tooling at the required target tablet weight of 250 mg.

Figure 3:
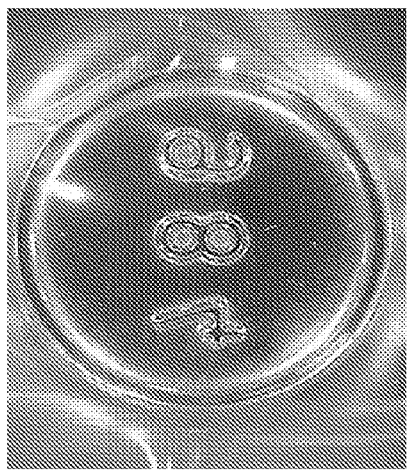
FIG. 3 shows photographic images displaying the minimal to lack of sticking and picking of the solid pharmaceutical composition of Example 4.
Figure 3:
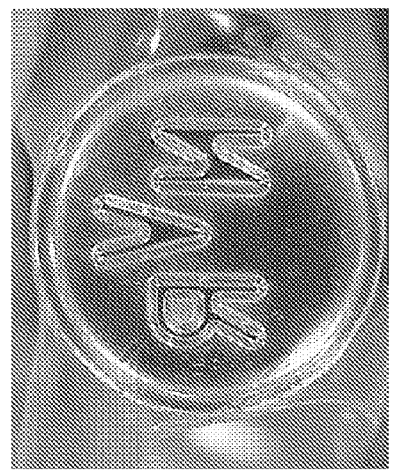

FIG. 3 provides photographic images displaying the minimal to lack of sticking and picking to the tablet punch of the solid pharmaceutical composition of this Example. This is a significant improvement as compared to the sticking and picking to the tablet punch of a previous direct compression pharmaceutical composition comprising the compound of formula (I) hydrochloride salt and the lubricant magnesium stearate vegetable (2% by weight relative to the weight of the overall composition), as shown in FIG. 1.

What is claimed is:

1. A roller compacted solid pharmaceutical composition comprising (a) the compound 4-(trifluoromethyl)-5-(2,6-dimorpholinopyrimidin-4-yl)pyridin-2-amine or a pharmaceutically acceptable salt thereof, (b) sodium stearyl fumarate, and (c) optionally at least one additional pharmaceutically acceptable carrier.

2. The roller compacted solid pharmaceutical composition according to claim 1, wherein the compound 4-(trifluoromethyl)-5-(2,6-dimorpholinopyrimidin-4-yl)pyridin-2-amine or a pharmaceutically acceptable salt thereof is present in an amount ranging from about 15% to 60% by weight of relative to the total weight of the overall composition.

3. The roller compacted solid pharmaceutical composition according to claim 1 or 2, wherein sodium stearyl fumarate is present in an amount ranging from about 3% to 8% by weight relative to the total weight of the overall composition.

4. The roller compacted solid pharmaceutical composition according to claim 1, wherein the pharmaceutical composition contains a plurality of granules having an internal phase and an external phase, and wherein said internal phase and external phase of the granules both include sodium stearyl fumarate.

5. The roller compacted solid pharmaceutical composition according to claim 1, wherein the pharmaceutical composition comprises at least one additional pharmaceutically acceptable carrier selected from a diluent, a disintegrant, a glidant, or a combination thereof.

6. The roller compacted solid pharmaceutical composition according to claim 1, wherein the pharmaceutical composition comprises the compound 4-(trifluoromethyl)-5-(2,6-dimorpholinopyrimidin-4-yl)pyridin-2-amine or a pharmaceutically acceptable salt thereof is present in an amount ranging from about 15% to 60% by weight relative to the total weight of the overall composition, sodium stearyl fumarate is present in an amount ranging from about 3% to 8% by weight relative to the total weight of the overall composition, and at least one additional pharmaceutically acceptable carrier selected from a diluent present in an amount from about 40% to about 70% by weight of the composition, a disintegrant present in an amount from about 2% to about 15% by weight of the composition, a glidant present in an amount from about 0.1% to about 4% by weight of the composition, or a combination thereof.

7. The roller compacted solid pharmaceutical composition according to claim 5 or 6, wherein the diluent is selected from microcrystalline cellulose, mannitol, or a combination thereof.

8. The roller compacted solid pharmaceutical composition according to claim 5 or 6, wherein the disintegrant is crospovidone.

9. The roller compacted solid pharmaceutical composition according to claim 5 or 6, wherein the glidant is colloidal silicon dioxide.

10. The roller compacted solid pharmaceutical composition according to claim 1 wherein the pharmaceutical composition shows an in vitro dissolution of the compound 4-(trifluoromethyl)-5-(2,6-dimorpholinopyrimidin-4-yl) pyridin-2-amine or a pharmaceutically acceptable salt thereof of 90% or more in 30 minutes or less.

11. The roller compacted solid pharmaceutical composition according to claim 1, wherein the solid pharmaceutical composition is in the form of a tablet.

12. A method for the treatment of cancer comprising administering a roller compacted solid pharmaceutical composition according to claim 1 comprising a therapeutically effective amount of the compound 4-(trifluoromethyl)-5-(2,6-dimorpholinopyrimidin-4-yl)pyridin-2-amine or a pharmaceutically acceptable salt thereof to a patient suffering from such cancer.

13. The method according to claim 12, wherein the cancer is selected from the group consisting of lung cancer, breast cancer, prostate cancer, pancreatic cancer, colon and rectum, thyroid cancer, liver and intrahepatic bile duct cancer, hepatocellular cancer, gastric cancer, glioma/glioblastoma, endometrial cancer, melanoma, kidney and renal pelvic cancer, urinary bladder cancer, uterine corpus cancer, uterine cervix cancer, ovarian cancer, multiple myeloma, esophageal cancer, neuroendocrine tumor, leukemia, lymphoma, brain cancer, head and neck cancer, small intestinal cancer, melanoma, and villous colon adenoma.

14. A process for the manufacture of a solid pharmaceutical composition according to claim 1 comprising the steps of roller compacting the compound 4-(trifluoromethyl)-5-(2,6-dimorpholinopyrimidin-4-yl)pyridin-2-amine or a pharmaceutically acceptable salt thereof together with sodium stearyl fumarate and optionally at least one additional pharmaceutically acceptable carrier, milling the compacted material to form a plurality of granules, and blending the granules with sodium stearyl fumarate and optionally at least one additional pharmaceutically acceptable carrier, and optionally compressing the final blend into a tablet.

* * * * *